United States Patent [19]
Bodicky

[11] Patent Number: 5,269,755
[45] Date of Patent: Dec. 14, 1993

[54] CATHETER WITH OUTER MEMBRANE MEDICAMENT DELIVERY SYSTEM

[75] Inventor: Raymond O. Bodicky, Oakville, Mo.

[73] Assignee: Sherwood Medical Company, St. Louis, Mo.

[21] Appl. No.: 943,850

[22] Filed: Sep. 11, 1992

[51] Int. Cl.$^5$ ............................................. A61M 29/00
[52] U.S. Cl. ......................................... 604/53; 604/96
[58] Field of Search .................................. 604/96-103, 604/51-56, 265, 246; 606/192, 194

[56]  References Cited
U.S. PATENT DOCUMENTS

| | | | |
|---|---|---|---|
| 4,932,958 | 6/1990 | Reddy et al. ................. | 604/54 X |
| 5,087,244 | 2/1992 | Wolinsky et al. .............. | 604/53 |
| 5,098,381 | 3/1992 | Schneider ..................... | 604/96 |
| 5,100,383 | 3/1992 | Lichtenstein .................. | 604/96 |

*Primary Examiner*—John D. Yasko
*Attorney, Agent, or Firm*—Andrew J. Beck; Montgomery W. Smith; Curtis D. Kinghorn

[57]  ABSTRACT

A catheter is disclosed having an outer sheath made of a porous polymer material such as expanded polytetrafluoroethylene (ePTFE). The sheath has a porosity to allow anti-microbial or anti-bacterial medicament or other medicaments or liquids to pass through the sheath. A medicament lumen is provided passing through the elongated tube of the catheter from the catheter's proximal or out of patient end to openings along the catheter tube wall. Medicament is passed from the proximal end of the catheter through the medicament lumen and expelled through the openings into the area between the sheath and the catheter's main tube. There, the medicament or other liquid passes through the sheath into contact with the patient's body lumen. In the preferred embodiment, the catheter is a Foley urinary catheter.

32 Claims, 4 Drawing Sheets

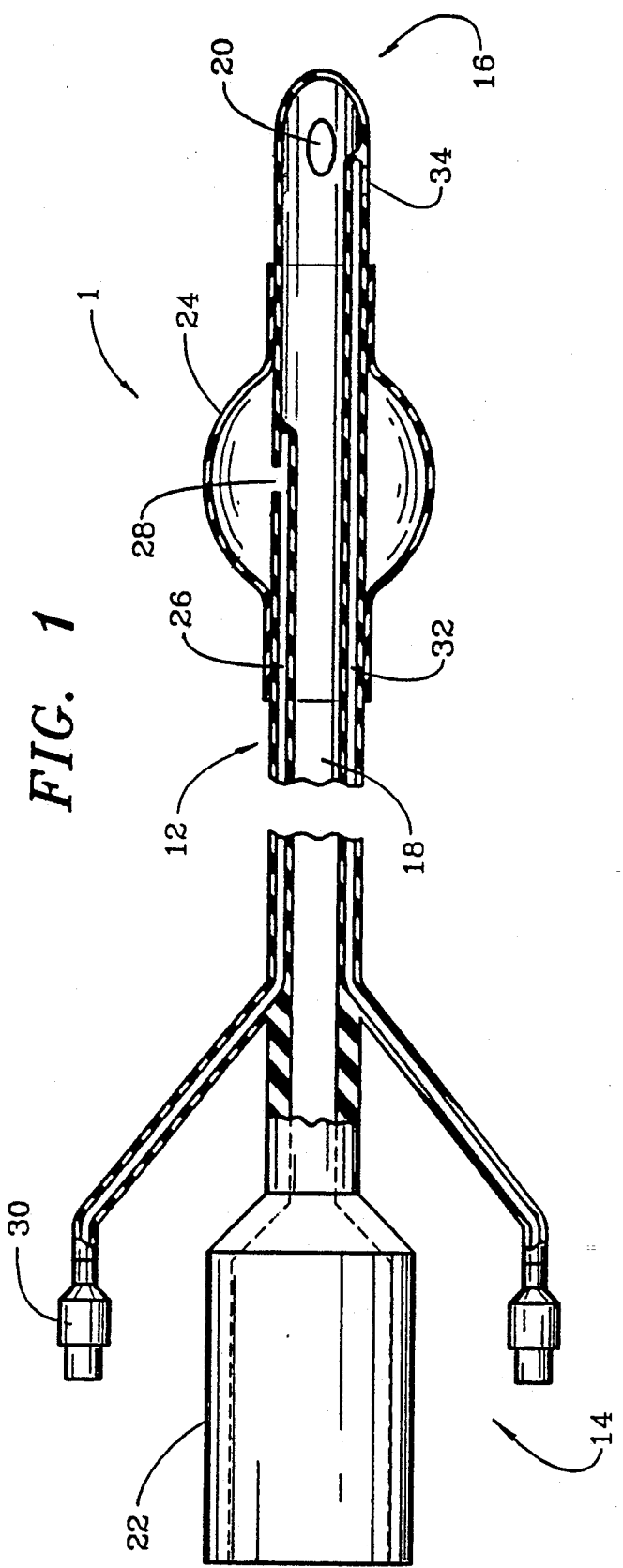
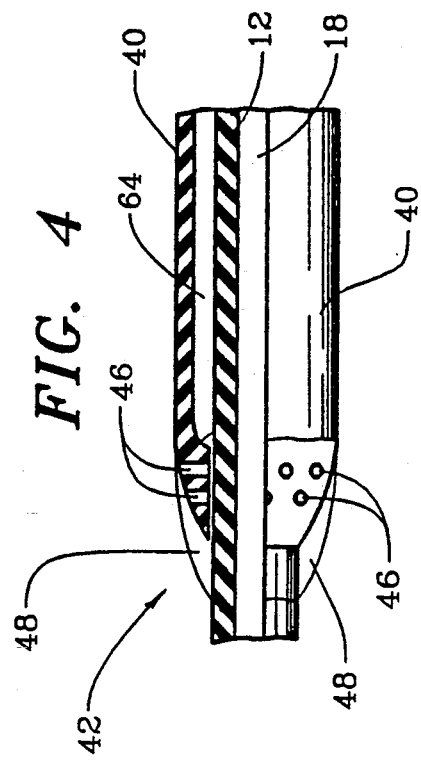
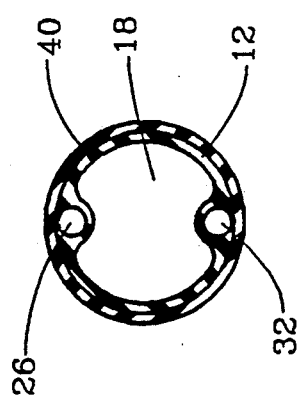

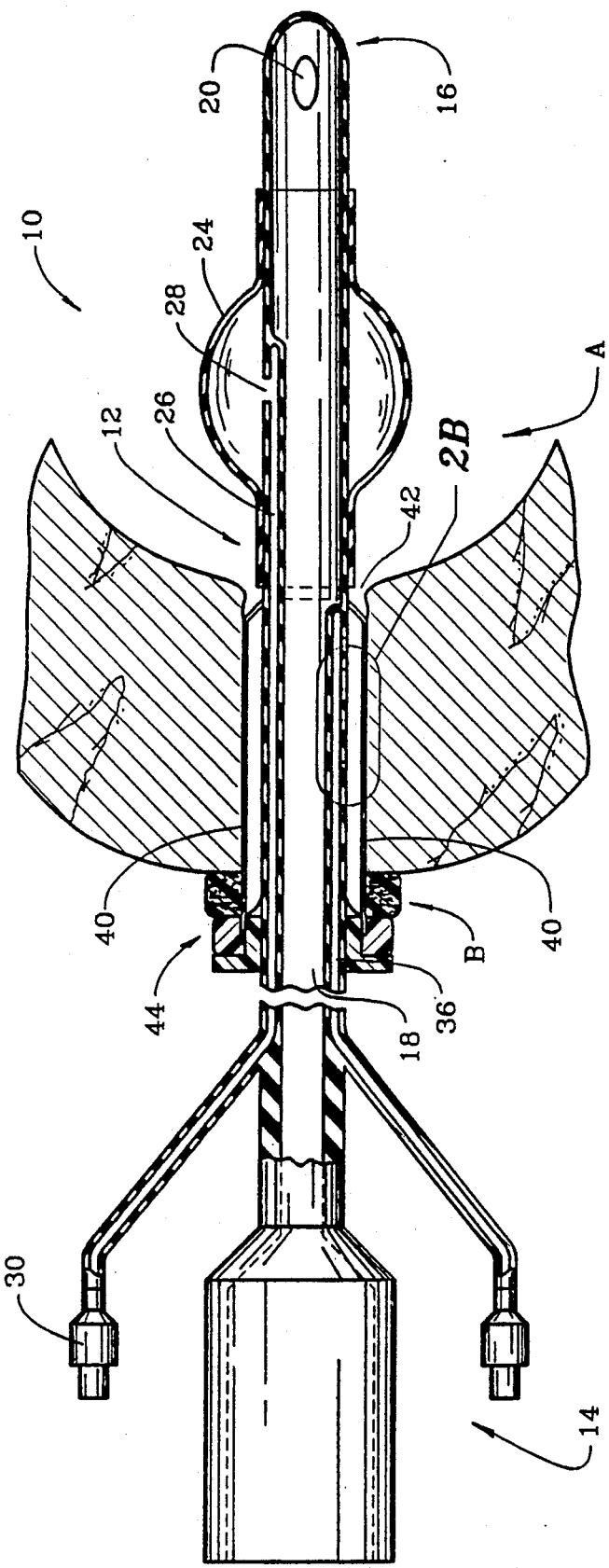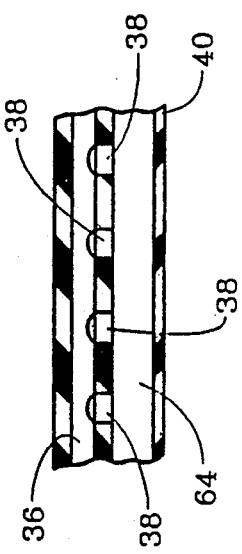

CATHETER WITH OUTER MEMBRANE MEDICAMENT DELIVERY SYSTEM

BACKGROUND OF THE INVENTION

1. Field of the Invention

The instant invention relates to catheters and more particularly to a urinary Foley catheter having an outer membrane which reduces irritation to the urethra caused by the catheter and allows for medicament, particularly antimicrobial or anti-bacterial medicament, or other liquids to be placed in the urethra through the membrane while the catheter is in place in the patient's urethra.

2. Description of Related Art

Urethral catheters are known that are placed within a patient's lower urinary tract. One type of urethral catheter is a retention catheter. Retention catheters connect the patient's bladder to the meatus of the patient to continuously remove urine from the patient's bladder. One type of urinary retention catheter is a Foley catheter.

As shown in FIG. 1, a typical Foley catheter 1 consists of an elongated tube 12 having a proximal end 14 and a distal end 16. A main lumen 18 extends from the proximal end 14 to the distal end 16. The catheter 1 is placed through the patient's urethra so that the distal end 16 extends into the patient's bladder and the proximal end remains outside the patient's body. The distal end 16 has an inlet opening 20 to allow urine to pass into the inlet opening 20 and through main lumen 18 of the elongated tube 12. The main lumen 18 extends to a connecting funnel 22 at the proximal end 14 which allows the urine to pass into a collection bag.

Foley catheters have a means for retaining them in position within the patient's bladder and urethra in the form of an inflatable balloon 24 located at the distal end 16 of the elongated tube 12 proximal to the inlet opening 20. An inflation lumen 26 connects the balloon 24 to the proximal end 14 of the catheter 10 so that a liquid may be passed under pressure through the inflation lumen 26, through inflation outlet 28 into balloon 24 to expand the balloon 24. A valve 30, such as is well known in the art, is also provided to maintain the liquid under pressure so that the balloon 24 remains inflated.

In operation, the distal end 16 of the catheter 1 is pushed through a patient's urethra into the patient's bladder a sufficient distance so that the balloon 24 is also within the bladder. The balloon 24 is then expanded within the patient's bladder to secure the catheter against movement in the proximal direction through the urethra. In a urethral catheter including such a balloon 24, the cross-section of the elongated tube 12 includes a main lumen 18 through which urine passes and an inflation lumen 26, typically smaller than the main lumen 18, through which the liquid passes from the proximal end 14 of the catheter to the balloon 24 for inflating the balloon 24.

In another embodiment of the catheter, an additional medicament lumen 32 is provided which extends from the proximal end 14 of the catheter to an outlet 34 located distal to the balloon 24. When this catheter is placed within the patient's urethra and retained in position in the patient's bladder, this outlet 34 is within the patient's bladder. Typically, medicaments are passed through this lumen 32 into the patient's bladder.

Recent studies have shown that hospital acquired or "nosocomial" urinary tract infections (UTI) affect about 900,000 Americans annually. J. R. Johnson, P. L. Roberts, R. J. Olsen, K. A. Moyer, and W. E. Stann, Prevention of Catheter Associated Urinary Tract Infection with a Oxide-Coated Urinary Catheter Clinical and Microbiologic Correlates, 162 Journal of Infectious Diseases, 1145–1150 (1990). Many of these UTIs are acquired in hospitals with the result that UTIs account for about 40% of all hospital acquired infections. Id. Of the UTIs acquired in hospitals, about 80% are catheter associated. Id. These hospital related UTIs prolong hospital stay by an average of 2.4 to 4.5 days and increase the hospital cost by $558.00 per episode. Id. If the percent of catheter associated UTIs could be reduced to 0, the annual saving in hospital cost alone could be reduced by $401,760,000.00.

An additional problem with UTIs associated with catheter use is that 1–3% of these patients develop bacteremia. Bacteremia is a potentially mortal disease. Therefore, it is clearly desirable to reduce the possibility of developing bacteremia.

A source of the catheter related UTIs is suspected to be bacteria progressing from the patient's meatus through the peri-urethral space into the bladder. One method in the prior art for attempting to prevent bacterial caused UTIs is disclosed in U.S. Pat. No. 4,773,901 to Norton. In the Norton patent, the urinary catheter is coated with silver oxide to kill bacteria which may find its way down the patient's periurethral space. However, for many applications, the device of the Norton patent has not proved to be totally effective. As a result, in these applications, a substantial probability of acquiring a UTI still exists when using the Norton device.

It is believed that the number of UTIs resulting from catheter use could be significantly reduced if antimicrobial material could be placed along the urethra to prevent the colonization and passage of the bacteria as desired while the catheter is in place within the patient's urethra.

SUMMARY OF THE INVENTION

A catheter is provided having an outer sheath made of a porous polymer material such as expanded polytetrafluoroethylene (ePTFE). The sheath has a porosity to allow anti-microbial or anti-bacterial medicament or other medicaments or liquids to pass through the sheath. A medicament lumen is provided passing through the elongated tube of the catheter from the catheter's proximal or out of patient end to openings along the catheter tube wall. Medicament is passed from the proximal end of the catheter through the medicament lumen and expelled through the openings into an area between the sheath and the catheter's main tube. There, the medicament or other liquid passes through the sheath into contact with the patient's body lumen.

In the preferred embodiment, the catheter is a Foley urinary catheter. However, the catheter may be used in urethral catheters that operate in the upper urinary tract as well as those, such as Foley catheters, which operate in the lower urinary tract. The catheter may be used as well in other catheters such as I.V. catheters, angiographic catheters or dialysis-type catheters to name but a few.

In all such cases, a catheter, such as is commonly used in the desired medical field, is modified by the addition of a sheath of ePTFE or similar material and a means to pass the desired liquid or medicament through the catheter to the area between the main tube of the catheter and the sheath. Of course, the porosity of the ePTFE or similar material is chosen to allow the desired medicament or other liquid appropriate for the catheter to pass therethrough.

Consequently, it is an object of the instant invention to provide a urethral catheter, and more particularly a Foley catheter, that significantly reduces the incidents of UTIs.

It is another object of the instant invention to provide a urethral catheter, and more particularly a Foley catheter, that places medicaments, particularly antibacterial medicaments, along the patient's urethra while the catheter is in position in a patient's urethra.

It is a further object of the instant invention to provide a urethral catheter, particularly a Foley catheter, that has reduced surface friction to reduce irritation to the patient's urethra resulting from relative movement of the catheter and the urethra while the catheter is placed into and is afterwards indwelling in the patient's urethra.

It is another object of the instant invention to provide a catheter, particularly a Foley catheter, that minimizes irritation to the patient's urethra caused by catheter movement resulting from patient movement.

It is another object of the instant invention to provide a catheter that places medicaments or other fluids along the outer surface of the tube of the catheter.

These and other objects of the instant invention will become obvious from the description of the invention contained herein and more particularly with reference to the following detailed description of the invention and the drawings where like elements are referred to by like reference numbers.

BRIEF DESCRIPTION OF THE DRAWINGS

FIG. 1 is a side cutaway view of a prior art Foley catheter.

FIG. 2A is a side cutaway view of a Foley catheter made according to the instant invention shown in place within a patient's urethra and bladder.

FIG. 2B is an enlarged view of the area of the openings shown in FIG. 2A.

FIG. 3 is a cross-sectional view of the catheter of FIG. 2 through line 3—3.

FIG. 4 is a quarter sectional view of the bond area where the ePTFE material is bonded to the elongated tube.

DETAILED DESCRIPTION OF THE INVENTION

Figure 5:
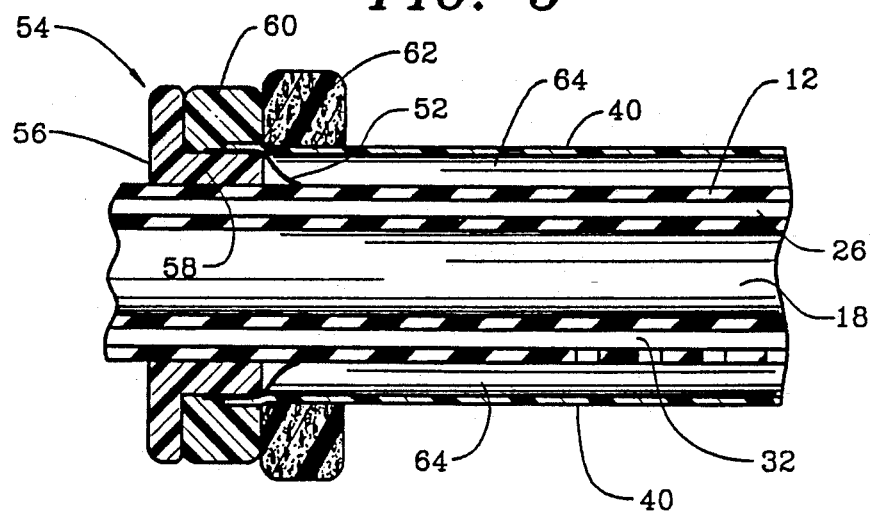
FIG. 5 is a side cutaway view of the seal of the invention of FIG. 2.

According to the preferred embodiment of the instant invention, a Foley catheter is shown in FIG. 2A generally labelled 10. Insofar as the catheter of FIG. 2 is similar to the catheter described above and shown in FIG. 1, similar elements are referred to by like reference numbers.

The catheter 10 has an elongated tube 12 connecting the patient's bladder A with the exterior of the patient's urethra B. The elongated tube 12 has a proximal end 14 that remains outside of the patient's body and a distal end 16 that is placed in a patient's bladder A. The elongated tube 12 includes a main lumen 18 extending from an inlet opening 20, located at the distal end 16 of the catheter 10, to the proximal end 14 of the catheter. Inlet opening 20 allows urine to pass from the patient's bladder A into the main lumen 18.

An inflation lumen 26 extends through the elongated tube 12 connecting a source of fluid located exterior to the patient's urethra (not shown) at the proximal end 14 to a balloon 24 attached at the distal end 16 of the catheter. Inflation lumen 26 terminates in an inflation outlet 28 that allows inflation lumen 26 to fluidly communicate with the interior of balloon 24. As is well known in the art, the balloon 24 preferably surrounds the elongated tube 12 and is located proximal to the inlet opening 20.

The details of the structure and operation of the balloon 24 and inflation lumen 26 is not given herein as it is well known to those skilled in the art. The critical function of the balloon 24 and inflation lumen 26 being that the catheter 10 is held in place within the patient's urethra by their action. When the catheter 10 is placed in the patient's urethra, fluid is passed along lumen 26 through inflation outlet 28 into balloon 24 to inflate the balloon 24 within the patient's bladder. The inflated balloon 24 contacts the inner surface of the patient's bladder A to hold the catheter 10 in place within the patient's bladder and to prevent proximal movement of the catheter 10 once it has been placed in position in the patient's urethra.

A valve 30 is provided at the proximal end of inflation lumen 26 to close inflation lumen 26 under pressure so that balloon 24 will remain inflated after being initially inflated to hold catheter 10 in position. At an appropriate time, the valve 30 is opened so that the liquid under pressure may be released from inflation lumen 26 and balloon 24 thereby deflating balloon 24.

In the invention, unlike the prior art catheter described above, a medicament lumen 36 is placed in the catheter 10 extending from the proximal end 14 of the catheter to an area of the elongated tube 12 proximal to the balloon 24. Medicament lumen 36 terminates proximal to the balloon 24 in a series of openings 38 which allow medicament introduced into lumen 36 at the proximal end 14 of the catheter to pass through lumen 36 and be expelled through openings 38.

As stated, medicament lumen 36 ends at its distal end with openings 38. Openings 38 may be holes of roughly circular or other geometric shape, but may also be slits which would then require pressure in medicament lumen 36 in order to open the slits and allow the medicaments to pass out of lumen 36. The pressure would be preferably applied through a syringe attached to the proximal end of medicament lumen 36. Openings 38 should not be placed further proximally than where the patient's urethra ends so that the medicament or other liquid will not leak out of the device outside the patient's urethra.

Although the medicament lumen 36 in the preferred embodiment of the invention differs from the medicament lumen 32 described above in connection with the prior art catheter, the medicament lumen 32 described above may also be used in addition to the preferred embodiment of the medicament lumen 36 of the instant invention.

A cylindrical sheath 40 of porous expanded polytetraflouroethylene (ePTFE) or similar material is placed around the elongated tube 12. A cylindrical medicament space 64 is formed between ePTFE sheath 40 and tube 12. The original method for making such porous expanded polytetraflouroethylene (ePTFE) is disclosed in U.S. Pat. No. 3,953,566 issued to R. W. Gore on Apr. 27, 1976. Many subsequent modifications and improvements of the original method have been made as are well understood by those skilled in the art.

Figure 7:
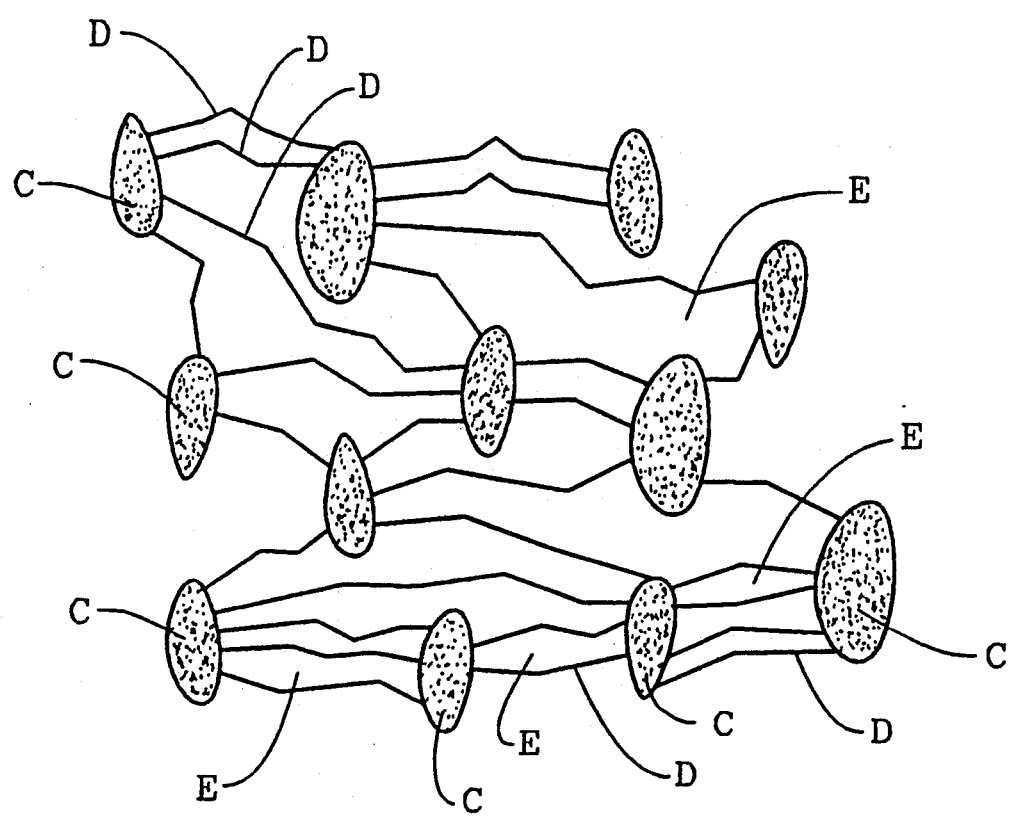
FIG. 7 is a schematic view of the nodes and fibrils of the ePTFE material used in the instant invention.

As shown in FIG. 7, in the ePTFE material, a microstructure of nodes C connected by fibrils D is formed. Substantially all of the fibrils D are bent into a bent or "wavy" shape. Fibrils D are resilient so that fibrils D change from a "wavy" shape to a straight shape as the nodes C attached to the ends of fibrils D are moved apart. Nodes C are moved away from each other as ePTFE sheath 40 is stretched. Conversely, after ePTFE sheath 40 has been stretched, when nodes C are moved together as ePTFE sheath 40 is compressed, fibrils D assume their "wavy" shape. ePTFE sheath 40 may be compressed beyond the point where the resilient fibrils D are stretched. Further compression of ePTFE sheath 40 causes fibrils D to "kink" more than they are usually bent.

Pores E are formed between the interconnected nodes C and fibrils D. The size of pores E is a function of whether fibrils D are stretched, relaxed or compressed between nodes C which is in turn a function of whether ePTFE sheath 40 is stretched or compressed. ePTFE material for the ePTFE sheath 40 is chosen to have pore sizes of pores E appropriate to allow the desired medicament or other liquid to pass therethrough. The chosen pore size of the pores E of the ePTFE material is a function of the viscosity of the medicament or other liquid as well as the injection pressure, if any, applied to the medicament or other liquid.

Currently, ePTFE material is available with pore sizes from about 5 to 100 micrometers. However, with ePTFE material made according to current technology, ePTFE material having large pore sizes might crush under the pressures present in the patient's urethra due to the age, sex and physical condition of the patient and the viscosity and other properties of the medicament or other fluid. This crushing of the ePTFE material renders it unsuitable for its intended purpose here. However, if technology improves so that ePTFE material becomes available with large pore sizes that are sufficiently rigid not to collapse yet performs all the other functions of ePTFE material as described herein, this improved material could be used according to the teachings contained herein.

The ePTFE sheath 40 is attached at its distal end to the elongated tube 12 at a distal attachment point 42 proximal to the balloon 24 but distal to openings 38. The ePTFE sheath 40 extends from this distal attachment point 42 to a sliding seal 44 located along the elongated tube 12 distal to the proximal end 14 of the catheter 10. In operation, seal 44 is moved into contact with the meatus of the patient so that the ePTFE sheath 40 extends from the meatus of the patient to the distal attachment point 42 proximal to the balloon 24 along the patient's urethra.

The ePTFE material performs several functions. First, the ePTFE material of sheath 40 has sufficient porosity to the desired medicament or other liquid to allow the medicament or other liquid expelled through openings 38 to pass through sheath 40. The medicament or other liquid introduced into the medicament lumen 36 at the proximal end 14 of the catheter 10 and expelled through the openings 38 passes through the cylindrical ePTFE sheath 40 into the patient's peri-urethral space. In this way, while the catheter 10 is in place in the patient's urethra, medicament, particularly an antimicrobial or anti-bacterial medicament, or other liquid is introduced to the patient's urethra as desired in order to prevent UTIs or provide other desired treatment.

A further use of the ePTFE material is to provide a reduced friction surface for the catheter in contact with the patient's urethra. A property of the ePTFE material is that it has a relatively low coefficient of friction compared to the coefficient of friction for the material of most catheters. Encasing the main lumen 12 in ePTFE material allows greater ease in introducing the catheter through the patient's urethra because of the reduced friction between the ePTFE material and the patient's urethra. Because of the reduced friction aspect of the ePTFE material, as the patient moves or as the urethra expands or contracts, there is a greatly reduced frictional contact between the ePTFE material and the patient's urethra. This greatly reduces the urethra's irritation and consequent susceptibility to UTIs compared to prior art urethral catheters.

An additional property of ePTFE material is that it is stretchable and contracts without bunching or rippling. Because of the reduced friction and stretchable aspects of the ePTFE material, as the patient moves or as the urethra changes in length, the ePTFE material has the ability to be expanded or contracted as needed to keep the seal 44 in contact with the meatus.

As stated above, the ePTFE material is attached at its distal attachment point 42 to the main tube 12 at a position proximal to the balloon 24. The ePTFE material is preferably mechanically bonded to the main tube 12. Geometrically staggered holes 46 or slits, as shown in FIG. 4, are placed through the walls of the ePTFE sheath 40 within the desired bond area at the distal attachment point 42. The holes 46 may be made by a mechanical process such as punching, cutting or drilling. In addition, the holes 46 may be made by other processes including chemical or heat treatment or other treatments or processes that increase the porosity of the ePTFE material in the desired area to produce holes. Regardless of the method used to make holes 46, the key is to provide openings through the ePTFE material.

An encircling silicone adhesive 48 is preferably applied to the main tube 12 at the area of the distal attachment point 42. Although a silicone adhesive is the preferred adhesive, other adhesives such as polyurethane on a polyurethane catheter could be used.

The distal end of the ePTFE sheath 40 is placed over the adhesive 48 so that the holes 46 are over the adhesive 48. An additional layer of adhesive 48 is applied over holes 46. The adhesive 48 moves within the holes 46 or slits in the ePTFE material from both sides of holes 46 to produce a mechanical bond.

The seal 44 attached to the proximal end of the ePTFE sheath 40 allows the proximal end of the ePTFE sheath 40 to be positioned at various places along the tube 12 of the catheter 10 and constrains the medicament or other liquid within ePTFE sheath 40 at its proximal end. One embodiment of the seal 44 is shown in more detail in FIG. 5. The seal 44 shown in FIG. 5 not only positions the ePTFE sheath 40 along tube 12 and constrains the medicament or other liquid within ePTFE sheath 40, but also holds the ePTFE sheath 40 open. That is, seal 44 retains a nearly constant diameter for sheath 40 at its proximal end despite any pressure applied to the outer surface of the ePTFE sheath 40 by the patient's urethra.

Referring to FIG. 5, the ePTFE sheath 40 overlays the proximal end of an elastomer seal 52. Elastomer seal 52 extends entirely around and has a distal portion in contact with main tube 12. Elastomer seal 52 is preferably made of a semi-rigid elastomer material such as latex or silicone. The proximal end of elastomer seal 52 is in turn attached to an eyelet 54.

Eyelet 54 extends entirely around main tube 12 and includes an end wall 56 and a cylindrical main tube wall 58. The proximal end of elastomer seal 52 extends around and contacts the outermost surface of main tube wall 58 while a portion of elastomer seal 52 extends distal to main tube wall 58 along main tube 12. The distal end of elastomer seal 52 contacts the outer surface of main tube 12 so that frictional contact between elastomer seal 52 and main tube 12 positions seal 44 along main tube 12. End wall 56 is annular in shape and allows main tube 12 to pass through the center of the annular ring.

ePTFE sheath 40 is surrounded at seal 44 by a compression ring 60, such as is well understood in the art, which extends entirely around main tube wall 58 and contacts the distal side of end wall 56. Compression ring 60 keeps ePTFE sheath 40 from slipping off seal 44 by compression force directed toward main tube wall 58. As an alternative to compression ring 60, the ePTFE material may be bonded to elastomer seal 44 and eyelet 54.

In operation, seal 44 contacts the meatus to avoid bacteria contacting the ePTFE material itself. However, in order to avoid irritation of the meatal area, a pad 62 is preferably placed on the distal side of seal 44 to contact the meatal area. Pad 62 is preferably either a closed polyurethane or open foam, including an open foam saturated with antibiotics, having a low durometer that extends in an annular fashion around the outer surface of ePTFE sheath 40.

In the preferred embodiment of the invention, the sheath 40 is made of expanded ePTFE material. However, sheath 40 may also be made of any porous polymer material including but not limited to porous silicone polymers.

In use, the distal end 16 of catheter 10 is pushed through the urethra of the patient until the balloon 24 is located within the patient's bladder A. Thereafter, fluid is passed through the inflation lumen 26 to expand balloon 24. Valve 30 is set to close inflation lumen 26 under pressure so that balloon 24 will remain inflated.

Figure 6:
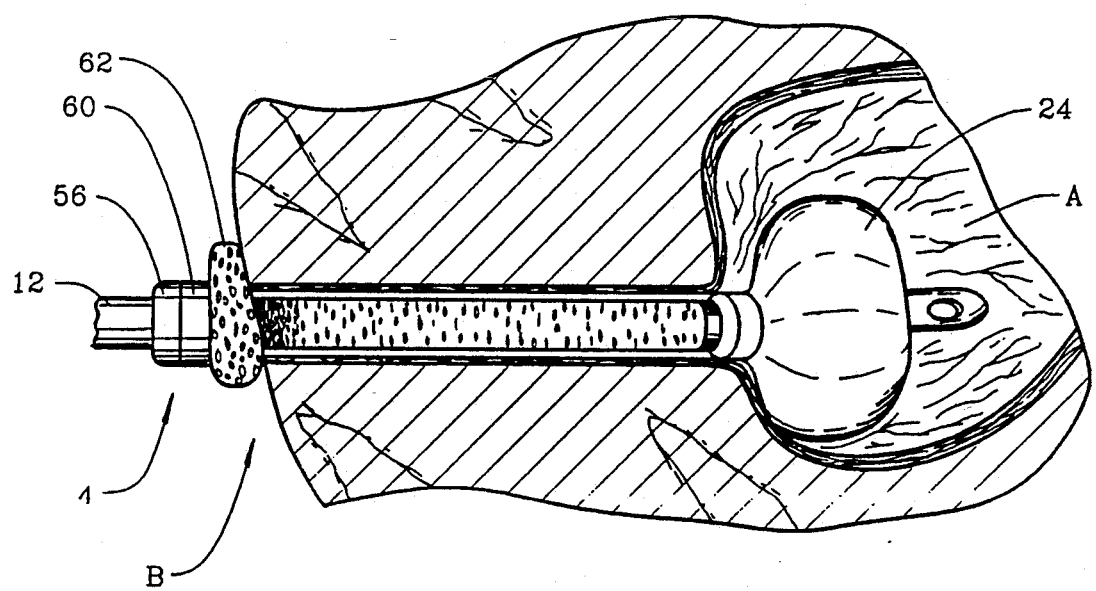
FIG. 6 is a side cut away view of the Foley catheter of FIG. 2A in position in a patient's urethra and bladder and showing the compression of the sheath along the axis of the catheter.

Seal 44 is then moved distally so that pad 62 is brought into contact with the meatal area. As shown in FIG. 6, as seal 44 is moved distally, the ePTFE sheath 40, attached to seal 44, is compressed along the axis of tube 12 near the area of the seal 44. When seal is moved in position near the meatal area, ePTFE sheath 40 near seal 44 will be compressed and the average pore sizes of pores E in sheath 40 near seal 44 will shrink as compared to the average pore sizes of the pores E of ePTFE sheath 40 along the ePTFE sheath 40 towards the distal attachment point 42.

Thereafter, the desired fluid or medicament may be placed through medicament lumen 36 where it is eventually expelled through openings 38. Then, the fluid or medicament passes into medicament space 64 between the outer surface of elongated tube 12 and the inner surface of ePTFE sheath 40. Thereafter, the medicament or other fluid will pass from medicament space 64 through the pores E in the ePTFE sheath 40 into the patient's urethra.

Because the average pore size of pores E near the distal attachment point 42 is somewhat larger than the average pore size of pores E of the ePTFE sheath 40 near seal 44, relatively more medicament or fluid will pass out of ePTFE sheath 40 along the ePTFE sheath 40 approaching distal attachment point 42 than will be passed through the ePTFE sheath near seal 44. This will prevent excessive fluid or medicament from leaking into the patient's urethra near seal 44 and consequently out of the patient's urethra near the meatus.

As mentioned above, anti-microbial or anti-bacterial medicament or other liquids are passed through the medicament lumen 36 and openings 38 to be expelled through the ePTFE sheath 40 into the patient's urethra. In the case of anti-microbial or anti-bacterial medicaments, these liquids kill microbes or bacteria, respectively, which may find its way into the patient's urethra. In another use of the instant invention in male patients, since catheter 10 passes through the prostrate gland, medicament specifically directed to the prostrate gland may be passed through medicament lumen 36 and out of ePTFE sheath 40 into contact with the prostrate gland in order to treat the gland.

Typically, Foley catheters have outside diameters of about 16 Fr. although other diameters may be used. However, with the addition of the ePTFE sheath 40, in order to maintain the 16 Fr. outside diameter or other desired diameter, the main tube 12 must have a correspondingly smaller outside diameter.

Because of a difference in length of urethras in males and females, it is intended that the instant invention be made in different lengths for males and females. For males, a Foley catheter of standard length having a ePTFE sheath 40 according to the instant invention in its most stretched length of about 7 to 9 inches long is preferred. For females, a Foley catheter of the length common for female use having a ePTFE sheath 40 according to the instant invention in its most stretched length of about 2 to 3 inches in length has been found to be effective. Although the instant invention has been described in connection with a main lumen 18, an inflation lumen 26 and a medicament lumen 36, as shown in the cross-sectional view of FIG. 3, additional lumens may be provided as desired so long as there is sufficient room within the main tube 12 to allow for the placement of additional lumens.

Further, although the instant invention has been described primarily in connection with the placement of an anti-microbial or anti-bacterial medicament into a patient's urethra, other medicaments or liquids may be placed in the patient's urethra as well. In one embodiment, if desired, the placement of the distal attachment point 42 and openings 38 may be moved to place a desired medicament or liquid at a desired location along the patient's urethra. For example, if a medicament is desired to be placed at a point midway between the patient's bladder and meatus, the distal attachment point 42 and openings 38 could be moved to a point slightly distal of the area to be medicated. In this way, the majority of the medicament or other liquid expelled from openings 38 and passing through the ePTFE sheath 40 will contact the desired area.

Although the preferred embodiment of the invention includes a Foley catheter, that is a retention catheter having a retaining balloon, any urethral catheter including those commonly referred to as "straight" or "intermittent" catheters may include the invention disclosed herein.

Further, the invention described herein may be applied to urethral catheters that operate in the upper urinary tract as well as those, such as Foley catheters, which operate in the lower urinary tract. This invention may be applied as well to medical catheters in general such as I.V. catheters, angiographic catheters or dialysis-type catheters to name but a few. In all such cases of applying the instant invention to catheters, a catheter such as is commonly used in the desired medical field is modified by the addition of a sheath of ePTFE or similar material and a means to pass the desired liquid or medicament through the catheter to the area between the main tube of the catheter and the sheath. Of course, the porosity of the ePTFE or similar material is chosen to allow the desired medicament or other liquid appropriate for the catheter to pass therethrough.

The invention above has been described in connection with specific embodiments. It is to be understood however that the particular descriptions contained herein is for the purpose of illustration and not for the purpose of limitation. Changes and modifications may be made to the description contained herein and still be within the scope of the claimed invention. Further, obvious changes and modifications will occur to those skilled in the art.

I claim

1. A catheter having a distal end to be placed in a patient's body and a proximal end, the catheter having a tube with a main lumen extending from the substantially the proximal end to substantially the distal end of the catheter, the catheter including:
   a) a secondary lumen extending from substantially the proximal end to the substantially the distal end of the catheter;
   b) means for placing fluids within said secondary lumen at substantially the proximal end of the catheter;
   c) means, located along the tube, for expelling fluid within said secondary lumen to the outer surface of the tube; and,
   d) porous means, extending along, attached to and entirely encircling a length of the tube, for constraining the fluids expelled through said means for expelling between the tube and said means for constraining, said means for constraining also passing the fluids through the pores of said means for constraining to the outer surface of said means for constraining, said means for constraining having a distal and a proximal end, wherein said means for constraining is made from a material chosen from the group consisting of expanded polytetrafluoroethylene and porous expanded silicone polymer.

2. The catheter of claim 1 wherein said means for expelling fluid within said secondary lumen to the outer surface of the tube comprises holes extending through the tube from said secondary lumen to the outer surface of the tube.

3. The catheter of claim 1 wherein said means for expelling fluid within said secondary lumen to the outer surface of the tube comprises slits extending through the tube from said secondary lumen to the outer surface of the tube.

4. The catheter of claim 1 wherein said means for constraining is connected to the tube through a means for connecting the distal end of said means for constraining to the tube at a point distal to said means for expelling.

5. The catheter of claim 4 wherein said means for connecting the distal end of said means for constraining comprises;
   a first layer of adhesive applied to the outer surface of the tube at the point that said means for constraining is to be attached to the tube;
   a second layer of adhesive applied to the outer surface of the distal end of said means for constraining; and,
   wherein the distal end of said means for constraining overlays said first layer of adhesive and wherein adhesive from said first and second layers of adhesive passes through the pores of said means for constraining into binding contact with adhesive from said second and first layers of adhesive, respectively, to connect said means for constraining to the tube.

6. The catheter of claim 5 wherein the distal end of said means for constraining has connecting holes extending therethrough to facilitate movement of adhesive from said first and second layers of adhesive through said connecting holes into contact with said second and first layers of adhesive, respectively.

7. The catheter of claim 4 wherein said means for connecting includes means for connecting the proximal end of said means for constraining to the tube.

8. The catheter of claim 7 wherein said means for connecting the proximal end of said means for constraining to the tube comprises a seal attached to the proximal end of said means for constraining, said seal encircling the tube.

9. The catheter of claim 8 wherein said seal includes means for preventing fluids, expelled from said means for expelling, between the tube and said means for constraining from moving proximally beyond the proximal end of said means for constraining.

10. The catheter of claim 7 wherein said means for connecting the proximal end of said means for constraining to the tube includes means for maintaining the proximal end of said means for constraining at a nearly constant diameter.

11. The catheter of claim 7 wherein said means for connecting the proximal end of said means for constraining to the tube includes means for selectively positioning said means for connecting the proximal end of said means for constraining to the tube along the tube.

12. A urinary catheter having a distal end to be placed in a patient's lower urinary tract and a proximal end, the catheter having a tube with a main lumen extending from the substantially the proximal end to substantially the distal end of the catheter, the catheter including:
   a) a secondary lumen extending from substantially the proximal end to substantially the distal end of the catheter;
   b) means for placing fluids within said secondary lumen at substantially the proximal end of the catheter;
   c) means, located along the tube, for expelling fluid within said secondary lumen to the outer surface of the tube; and,
   d) porous means, extending along and entirely encircling a length of the tube, for constraining the fluids expelled through said means for expelling between the tube and said means for constraining, said means for constraining also passing the fluids through the pores of said means for constraining to the outer surface of said means for constraining, said means for constraining having a distal and a proximal end.

13. The catheter of claim 12 wherein said means for constraining comprises a porous polymer.

14. The catheter of claim 13 wherein said porous polymer is an expanded polytetrafluoroethylene material having a plurality of nodules and interconnecting fibrils.

15. The catheter of claim 13 wherein said porous polymer is a porous silicone polymer.

16. The catheter of claim 12 wherein said means for expelling fluid within said secondary lumen to the outer surface of the tube comprises holes extending through the tube from said secondary lumen to the outer surface of the tube.

17. The catheter of claim 12 wherein said means for expelling fluid within said secondary lumen to the outer surface of the tube comprises slits extending through the tube from said secondary lumen to the outer surface of the tube.

18. The catheter of claim 12 further including means for connecting said means for constraining to the tube.

19. The catheter of claim 18 wherein said means for connecting includes means for connecting the distal end of said means for constraining to the tube at a point distal to said means for expelling.

20. The catheter of claim 19 wherein said means for connecting the distal end of said means for constraining comprises:
   a first layer of adhesive applied to the outer surface of the tube at the point that said means for constraining is to be attached to the tube;
   a second layer of adhesive applied to the outer surface of the distal end of said means for constraining; and,
   wherein the distal end of said means for constraining overlays said first layer of adhesive and wherein adhesive from said first and second layers of adhesive passes through the pores of said means for constraining into binding contact with adhesive from said second and first layers of adhesive, respectively, to connect said means for constraining to the tube.

21. The catheter of claim 20 wherein the distal end of said means for constraining has connecting holes extending therethrough to facilitate movement of adhesive from said first and second layers of adhesive through said connecting holes into contact with said second and first layers of adhesive, respectively.

22. The catheter of claim 18 wherein said means for connecting includes means for connecting the proximal end of said means for constraining to the tube.

23. The catheter of claim 22 wherein said means for connecting the proximal end of said means for constraining to the tube comprises a seal attached to the proximal end of said means for constraining, said seal encircling the tube.

24. The catheter of claim 23 wherein said seal includes means for preventing fluids, expelled from said means for expelling, between the tube and said means for constraining from moving proximally beyond the proximal end of said means for constraining.

25. The catheter of claim 22 wherein said means for connecting the proximal end of said means for constraining to the tube includes means for maintaining the proximal end of said means for constraining at a nearly constant diameter.

26. The catheter of claim 22 wherein said means for connecting the proximal end of said means for constraining to the tube includes means for selectively positioning said means for connecting the proximal end of said means for constraining to the tube along the tube.

27. The catheter of claim 22 further including means, attached to the distal side of said means for connecting the proximal end of said means for constraining to the tube, for preventing irritation of the meatus of the patient when the means for connecting the proximal end of said means for constraining to the tube is in contact with the patient's meatus.

28. The catheter of claim 12 wherein said means for constraining has a length, in its most stretched configuration in the catheter used on males, of between about 7 to 9 inches.

29. The catheter of claim 12 wherein said means for constraining has a length, in its most stretched configuration in the catheter used on females, of between about 2 to 3 inches.

30. In a catheter having a distal end to be placed in a patient's body and a proximal end, the catheter having a tube with a main lumen extending from the substantially the proximal end to substantially the distal end of the catheter, the catheter including a secondary lumen extending from the substantially the proximal end to substantially the distal end of the catheter; means for placing fluids within the secondary lumen at substantially the proximal end of the catheter; means, located along the tube, for expelling fluid within the secondary lumen to the outer surface of the tube; and, porous means, extending along and entirely encircling a length of the tube, for constraining the fluids expelled through the means for expelling between the tube and the means for constraining, the means for constraining also passing the fluids through the pores of the means for constraining to the outer surface of the means for constraining, the means for constraining having a distal and a proximal end, a method of connecting the distal end of the means for constraining to the tube comprising the steps of:
   applying a first layer of adhesive to the outer surface of the tube at the point that the means for constraining is to be attached to the tube;
   overlaying the distal end of the means for constraining over said first layer of adhesive; and,
   applying a second layer of adhesive to the outer surface of the distal end of the means for constraining;
   whereby adhesive from said first and second layers of adhesive passes through the pores of the means for constraining into binding contact with adhesive from said second and first layers of adhesive, respectively, to connect the means for constraining to the tube.

31. The method of claim 30 further comprising the step of forming connecting holes through the distal end of the means for constraining to facilitate movement of adhesive from said first and second layers of adhesive through said connecting holes into contact with said second and first layers of adhesive, respectively.

32. A catheter having a distal end to be placed in a patient's body and a proximal end, the catheter having a tube with a main lumen extending from the substantially the proximal end to substantially the distal end of the catheter, the catheter including:

a) a secondary lumen extending from substantially the proximal end to substantially the distal end of the catheter;
b) means for placing fluids within said secondary lumen at substantially the proximal end of the catheter;
c) means, located along the tube, for expelling fluid within said secondary lumen to the outer surface of the tube;
d) porous means, extending along, attached to and entirely encircling a length of the tube, for constraining the fluids expelled through said means for expelling between the tube and said means for constraining, said means for constraining also passing the fluids through the pores of said means for constraining to the outer surface of said means for constraining, said means for constraining having a distal and a proximal end;
e) means for connecting the distal end of said means for constraining to the tube at a point distal to said means for expelling; and,
f) means for connecting the proximal end of said means for constraining to the tube, said means for connecting the proximal end comprising a seal attached to the proximal end of said means for constraining, said seal encircling the tube, said seal including means for preventing fluids, expelled from said means for expelling between the tube and said means for constraining, from moving proximally beyond the proximal end of said means for constraining, said seal including means for selectively positioning said means for connecting the proximal end of said means for constraining to the tube along the tube.

* * * * *